United States Patent [19]

Gancet et al.

[11] Patent Number: 4,855,233
[45] Date of Patent: Aug. 8, 1989

[54] PROCESS FOR CARRYING OUT ENZYMATIC REACTIONS IN AN ORGANIC SOLVENT

[75] Inventors: Christian Gancet, Billere; Claude Guignard, Habas; Philippe Fourmentraux, Pau, all of France

[73] Assignee: Societe Nationale Elf Aquitaine, France

[21] Appl. No.: 30,696

[22] Filed: Mar. 25, 1987

[30] Foreign Application Priority Data

Mar. 26, 1986 [FR] France ............................... 86 04352

[51] Int. Cl.$^4$ ........................... C12P 7/62; C12P 7/64
[52] U.S. Cl. ...................................... 435/135; 435/41; 435/134; 435/911; 435/939
[58] Field of Search ................ 435/134, 135, 174–182, 435/41, 183, 911, 939

[56] References Cited

U.S. PATENT DOCUMENTS

| | | | |
|---|---|---|---|
| 4,357,311 | 11/1982 | Schutt .................... | 435/179 |
| 4,514,500 | 4/1985 | Giaever et al. ............ | 435/948 |
| 4,622,294 | 11/1986 | Kung et al. .............. | 435/177 |
| 4,678,746 | 7/1987 | Jochim et al. ............ | 435/172.2 |

FOREIGN PATENT DOCUMENTS 0891765 11/1981 U.S.S.R. .............................. 435/134

OTHER PUBLICATIONS

Adlercreutz et al., "Oxygen Supply to Immobilized Biocatalysts, a Model Study*, " Acta Chemica Scand., B36(9), pp 651–653, 1982.

*Primary Examiner*—Robert J. Hill, Jr.
*Assistant Examiner*—Timothy M. McMahon
*Attorney, Agent, or Firm*—Ostrolenk, Faber, Gerb & Soffen

[57] ABSTRACT

Process for carrying out an enzymatic reaction, in which the substrate treated is in an organic liquid which is a fluorinated hydrocarbon, which can include halogens other than fluorine.

15 Claims, No Drawings

PROCESS FOR CARRYING OUT ENZYMATIC REACTIONS IN AN ORGANIC SOLVENT

The present invention relates to enzymatic reactions carried out in organic liquids, that is operations where a given substrate, in solution or dispersion in an organic solvent, is subjected to the action of an enzyme. It applies to various types of reactions which can be carried out with the aid of enzymes, in particular hydrolysis, including ester bonds, transesterifications, interesterifications, syntheses of esters or thioesters, amidations etc.

Up till now, the numerous known enzymatic reactions have taken place in aqueous media, but when the substrate to be treated is insoluble in water, as is the case for example with fatty materials, there will clearly be interest in operating in a medium capable of dissolving the substrate. Thus, it has been proposed to carry out the interesterification of fatty materials in petroleum ether which dissolves them (European Patent Application No. 0064855), but this solvent is flammable and rapidly combustible. Thus the choice of solvent is difficult, because it must be compatible with the enzyme, but must not interfere with its action. Recently, it has been found that certain mixtures of ethers and ketones are suitable, notably, for the hydrolysis of triglycerides (French Patent Application No. 8506388); a clear advance has thus been made, but this is still making use of flammable materials and these mixtures are poorly suitable for other reactions, particularly esterifications.

The present invention is based upon the discovery of a class of organic compounds which not only do not interfere with the action of numerous enzymes, but can even enhance their action; these compounds are non-flammable and non-explosive and are capable of dissolving various hydrophobic substances, in particular fatty materials.

Thus the process for carrying out enzymatic reactions in organic solvents according to the invention is characterised by the use of one or more fluorinated or halogenofluorinated hydrocarbons containing halogens other than fluorine.

In the following part of the present description, with a view to simplification, the organic liquids employed according to the invention to serve as the reaction medium for the enzyme are referred to as fluorinated hydrocarbons, but this term covers both compounds which are only fluorinated as well as those which also contain other halogens, in particular Cl and/or Br.

Numerous fluorinated aliphatic and aryl hydrocarbons are suitable for carrying out the invention. However, as it is preferable to employ relatively less viscous compounds, suited to the moderate temperatures at which enzymatic reactions take place, the preferred fluorinated derivatives are those of $C_1$ to $C_8$ hydrocarbons. In the class of fluorinated aliphatic hydrocarbons, the most suitable are from $C_1$ to $C_4$, while the aromatics are preferably from $C_5$ to $C_8$.

Among fluorinated aliphatic hydrocarbons, those corresponding to the overall general formula $C_nH_mF_pX_t$ are particularly suitable, where n is 1 to 8, m=0 to n, p is 1 to 18 and t=0 to 16, X being Cl or Br or possibly comprising Cl and Br atoms simultaneously.

Fluorinated compounds boiling below 100° C., some of them below 0° C., correspond to the same overall formula for n=1 to 4, m=0 to n, p=1 to 4 and t=0 to 6.

Among fluorinated hydrocarbons utilisable in the invention, the group known under the name "Freons" or "Foranes" are found, comprising refrigerant liquids. Even those having a boiling point below 0° C. can serve for carrying out the invention, provided operation takes place under pressure, which can be completely viable. A Table 1 of characteristics of some of the fluorinated solvents utilisable is given below by way of non-limitative examples. Reference can also be made to compounds such as: fluorodichloromethane, fluorodibromomethane, fluorodibromoethane, fluorotetrabromomethane, fluorotetrachloroethane, fluorotribromomethane, fluorotrichloroethane, fluorobromodichloroethane, difluoro-1-chloroethane, difluoro-1,1-dibromoethane, 1,2-difluoroethane, trifluoro-1,2-dibromomethane etc.

Trichlorofluoromethane, $CFCl_3$, and trichlorotrifluoroethane, $CClF_2-CFCl_2$, merit special mention because of their utility in the invention.

Among fluorinated aryl derivatives, a choice can be made for example from fluorobenzene, fluorochlorobenzenes, fluorotoluenes, difluorochlorotoluenes etc.

Most of the fluorinated compounds proposed according to the invention have in addition to the advantages of non-flammability and non-explosivity, the absence of toxicity, which is a very important property for preparations concerning foodstuffs, pharmacy and cosmetics. Table 2 further below, gives the limits of tolerable concentrations for man by respiratory ingestion, expressed in ppm and $mg/m^3$; this table compares the toxicity limits of 14 different volatile compounds with those of trichlorotrifluoroethane, a product of the type according to the invention; this confirms that the animal organism can tolerate more than 100 times as much of this chlorofluorinated hydrocarbon as compared with benzene or chloroform.

According to a variant of the invention, the fluorinated hydrocarbon is employed in association with another liquid, to form a mixed solvent, having a better dissolving power vis-à-vis the substrate to be treated, a suitable boiling point, a certain capacity for the absorption of water and/or other improved physical and physiochemical characteristics as compared with the components of the mixture taken separately.

TABLE 1

| | Characteristics of fluorinated solvents | | |
|---|---|---|---|
| Formula | "Freons" or "Foranes" N° | $\theta_{EB}$ °C.[a] | Vapour pressure 30° C.[b], bar |
| $CF_4$ | 14 | −128.0 | — |
| $CF_3Cl$ | 13 | −81.4 | 40 |
| $CF_2Cl_2$ | 12 | −29.8 | 7.4 |
| $CFCl_3$ | 11 | +23.8 | 1.3 |
| $CF_2ClBr$ | 12B1 | −4.0 | 3.3 |
| $CF_3Br$ | 13B1 | −57.8 | 18.2 |
| $CHClF_2$ | 22 | −40.8 | 11.9 |
| $CHF_3$ | 23 | −82.1 | |
| $CF_3CH_3$ | 116 | −78.2 | 40 |
| $CClF_2CF_3$ | 115 | −38.7 | 11 |
| $CClF_2CClF_2$ | 114 | +3.8 | 2.50 |
| $CClF_2CFCl_2$ | 113 | +47.6 | 0.54 |
| $CCl_2FCCl_2F$ | 112 | +92.8 | — |
| $CH_3CHF_2$ | 152 | −24.7 | — |
| $CF_3(CF_2)_5CF_3$ | — | +101 | — |

[a] absolute pressure 1 bar
[b] pressure value to maintain the solvent in the liquid state.

TABLE 2

Scale of toxicities compared with certain solvents (1982)

| Solvent | Tolerable concentration limit in air | |
|---|---|---|
| | ppm | mg/m$^3$ |
| Methyl bromide | 5 | — |
| Carbon tetrachloride | 5 | 35 |
| Chloroform | 10 | 50 |
| Benzene | 10 | 50 |
| Ammonia | 25 | — |
| Perchloroethylene | 50 | 335 |
| Trichloroethylene | 50 | 270 |
| White spirit | 100 | — |
| Methylene chloride | 100 | 350 |
| Hexane | 100 | 360 |
| 1,1,1-Trichloroethane | 350 | 1900 |
| Butane | 800 | — |
| Ethanol | 1000 | 1900 |
| Trichlorotrifluoroethane | 1000 | 7600 |
| Carbon dioxide | 5000 | 9000 |

Thus, use can be made of a mixture of one or several fluorinated hydrocarbons with liquids such as aliphatic or aryl hydrocarbons, alcohols, ketones, ethers, esters etc. For example, the fluorinated compounds cited above or those of Table 2 can be used in admixture with petroleum ether, hexane, octane, benzene, toluene, dioxane, acetone, methylethyl ketone, isopropanol, ethyl acetate etc., these compounds being mentioned only by way of non-limitative examples. Depending upon the compatibility of the mixed solvents, the proportion of the fluorinated compound is in general of the order of 20 to 95% by weight.

It is to be noted that, due to the non-flammability of various fluorinated compounds, the mixtures indicated above can gain considerably in safety, since they contain less inflammable compounds having explosive vapours.

While the fluorinated compounds according to the invention can be employed in various cases of free enzymes, these being dispersed in the organic liquid, a particularly interesting field for their application is where the enzyme is fixed to a substrate. This concerns both enzyme systems on mineral substrates, ion exchangers or polymers and also on natural tissues, such as mycelium, cellulosic plant substrates and others.

The fluorinated hydrocarbons used according to the invention are suitable in various known enzymatic techniques, particularly discontinuously, continuously in columns or reactors, on fluidized beds and others.

The range of uses of the invention is very large, because in general fluorinated hydrocarbons can be employed with all kinds of enzymes and substrates. When the latter are water-soluble, this application is not favoured, because it is generally economical to operate in aqueous media. By contrast, the invention acquires considerable interest in relation to enzymatic treatments of producs which are insoluble or slightly soluble in water; this is the case particularly with fats, oils, waxes, phospholipids, particularly lecithins, steroids, lipoproteins etc.

Thus, the invention applies to all classes of enzymes, proteases, oxydases, hydrolases, particularly esterases, lipases, phosphatases, transferases etc.

Particularly interesting industrial applications reside in the treatment of fatty materials with lipases with a view to effecting hydrolysis or the synthesis of ester bonds, interesterification or transesterification of fatty materials. This also applies to thioester or amide bonds.

The temperature and concentration conditions generally known in relation to enzymatic reactions are suitable in carrying out the present invention. Thus, the temperatures most often suitable are from 10° to 80° C. and particularly from 30° to 50° C. In the case of esterifications of fatty acids, the preferred acid concentrations range from 0.05 to 1.5M and most preferably from 0.1 to 1 mole/liter.

The non-limitative examples which follow illustrate the invention for different cases of enzymatic reactions of industrial interest. Most of the tests have been effected with the lipase produced by the fungus *Rhizopus arrhizus* (ATCC 24 563) and the mode of preparation of this enzyme follows.

The Rhizopus is cultivated in a fermenter in the following medium:
 colza oil: 20 g/l
 "Corn Steep Liquor": 50
 KH$_2$PO$_4$: 2
 KCl: 0.5
 NaNO$_3$: 0.5
 MgSO$_4$.7H$_2$O: 0.5

The initial pH is 4.6. Growth takes place for 3–5 days at 25°–30° C. The mycelium is then dried, washed with distilled water and dried again, either in a vacuum chamber at moderate temperature or by lyophilisation. The dry mycelium is degreased by extraction, then ground, screened and stored dry. The lipasic activity of the mycelium thus prepared ranges between 0.9 and 4 units/mg (on triolene in emulsion).

Examples 1 to 42 show various preparations using the lipase prepared as indicated above, except for Example 17 relating to the enzyme produced by *Geotrichum Candidum* cultivated in the same manner. Examples 29 to 42 give the results of a series of comparative tests showing the advantage of fluorinated hydrocarbons over various other organic liquids in the esterification of fatty acids.

EXAMPLES 1 TO 15

Esterification of oleic acid with various alcohols in trichlorotrifluoroethane.

In each case, use is made of 10 ml of solution of an alcohol and oleic acid, in Cl$_2$FC–CF$_2$Cl (Freon on Forane 113), in which are dispersed 0.1 or 0.2 g of dry devitalised mycelium of *Rhizopus arrhizus* prepared as indicated above, and respectively 0.1 or 0.2 g of molecular seive, for absorbing the water formed by the esterification. Thus depending upon the case, the proportion of the mycelium is 10 or 20 g per liter of reaction medium; it is equal to that of the molecular seive. The reaction takes place at 30° C. for the duration indicated for each case in the following results Table.

The Table gives the concentrations in alcohol and oleic acid in moles/liter.

| Ex. | Alcohol | Concentration in mol/liter: alcohol | Concentration in mol/liter: oleic acid | g of mycelium per l | Duration h | % Conversion of acid |
|---|---|---|---|---|---|---|
| 1 | methanol | 0.1 | 0.1 | 10 | 2.5 | 86 |
| 2 | " | 1 | 0.5 | 20 | 3 | 62 |
| 3 | ethanol | 0.1 | 0.1 | 10 | 2.5 | 91 |
| 4 | " | 1 | 0.5 | 20 | 3 | 70 |
| 5 | octanol | 0.1 | 0.1 | 10 | 2.5 | 83 |
| 6 | " | 1 | 0.5 | 20 | 3 | 73 |
| 7 | butanol | 1 | 0.5 | 20 | 3 | 76 |
| 8 | cinnamic alcohol | " | " | " | " | 76 |
| 9 | iso-amyl alcohol | " | " | " | " | 83 |
| 10 | octa-decanol alcohol | " | " | " | " | 75 |
| 11 | hexadecanol alcohol | " | " | " | " | 79 |
| 12 | oleic alcohol | " | " | " | " | 77 |
| 13 | decanol-1 | " | " | " | " | 78 |
| 14 | propanol-1 | " | " | " | " | 67 |
| 15 | glycerol | " | " | " | 18 | 62 |

It appears that the conversion is highest for the lowest concentrations, 0.1 mole/l, even after a very short time and with less mycelium, than for concentrations of 1 mole/l.

The process of the invention allows esterifications to achieve 62 to 91% of the acid with various alcohols, which constitutes a very interesting industrial result.

EXAMPLE 16

Operation was as in examples 7 to 14 with isopropanol as the alcohol and myristic acid in place of the oleic acid. The conversion of the acid was B 12%.

EXAMPLE 17

The mycelium of Rhizopus in Example 16 is replaced by that of *Geotrichum candidum*. Conversion of the fatty acid was 7.6%.

EXAMPLES 18 to 20

By proceeding as in Examples 1, 3 and 5 (concentrations of 0.1M, duration of 2½ hours) the Freon or Forane 113 was replaced by Freon or Forane 11, that is with trichlorofluoromethane, $CFCl_3$. The conversions of the oleic acid were thus:
 with octanol: 85.4%
 with decanol: 88.3
 with octadecanol: 86.9

EXAMPLE 21

Continuous Esterification

The reactor comprises two columns each containing 5.5 g of a devitalised mycelium of *Rhizopus arrhizus* per 10 ml of silica, separated by a column of a molecular seive serving as a drier. The dead space of the columns filled with the mycelium is of the order of 15 ml for a throughput of the order of 12 ml/h, which corresponds to a residence time of 75 min per column. The reaction mixture has the composition: oleic acid 0.5 M/l, octanol 0.5 M/l, solvent trichlorotrifluoroethane. The rate of conversion of the oleic acid is 96.3% continuously.

EXAMPLES 22 and 23

Thioesterification

The mode of operation is the same as in Example 15, that is the same as for Examples 6 to 14, but lasted for 18 hours, the alcohols being replaced by mercaptans. The rate of conversion of the oleic acid obtained was as follows:
 Ex. 22: with butane-thiol: 24%
 Ex. 23: with hexane-thiol: 23%.

EXAMPLE 24

Transesterification

The reaction mixture is constituted by 10 ml of trichlorotrifluoroethane (Freon or Forane 113) containing 1 g of tallow and 1 g of lauric acid. To this mixture is added 0.2 g of the mycelium of *R. arrhizus* and it is agitated at 30° C. for 20 hours. After separation of the mycelium, the mixture is isolated and analysed by gas chromatograhy using trimethylsilyl derivatives of the fatty acids. The proportion of fatty acids freed from the tallow by transesterification is 44.1%.

EXAMPLES 25 to 27

Amidation

The mode of operation is the same as in Examples 6 to 14 above, the alcohol being replaced by amines, viz. 0.1 mole of amine with 0.5 mole of oleic acid/liter; 20 g of the enzymatic mycelium/liter and the same amount of the molecular sieve. The fluorinated liquid is $Cl_2FC-CF_2Cl$. Conversions of the oleic acid are:
 Example 25: with dodecylamine: 81%
 Example 26: with ethanolamine: 28
 Example 27: with hexamethylenediamine: 14

EXAMPLE 28

Continuous methanolysis

The reactor is constituted by a column containing 5.6 g of the mycelium prepared as above and 10 ml of silica. The temperature is 30° C. and the residence time is 75 mins. The reaction mixture comprises trichlorotrifluoroethane (Freon or Forane 113), containing by weight of the mixture 11.4% of refined tallow, 2.5% of methanol and 86.1% of this fluorinated compound. Operating continuously, the proportion of fatty acids liberated in the form of the methyl esters attained 7.9%.

EXAMPLES 29 to 42

Esterification with various solvents

For comparison, the esterification of n-octanol with oleic acid is effected under the same conditions with a series of different solvents for the fatty acid. The conditions are those of Examples 1, 3 and 5, namely concentrations/liter of 0.1 mole per acid as for the alcohol, 10 g of the mycelium of *R. arrhizus* and 10 g of the molecular sieve; 30° C., duration 2½ hours. The percent conversions of oleic acid found are as follows:

| Example No | Solvent | % Conversion |
|---|---|---|
| 29 | Trichlorotrifluoroethane (F113) | 83 |
| 30 | Trichlorofluoromethane (F11) | 85.4 |
| 31 | Tetrachlorodifluoroethane (F112) | 85 |
| 32 | Perfluoroheptane | 81 |
| 33 | Diphenylether | 76 |
| 34 | Dibutyl phthalate | 68 |
| 35 | Methyl-t-butyl-ether | 56.6 |
| 36 | Dimethoxy-propane | 44.9 |
| 37 | Tributyl phosphate | 44.2 |
| 38 | 1,2-diethoxy-ethane | 19.4 |
| 39 | Dioxane | 11.3 |
| 40 | Methyl-octyl ketone | 0 |
| 41 | Dimethyl-formamide | 0 |
| 42 | Dimethyl-sulphoxide | 0 |

It can be seen that the fluorinated hydrocarbons of Examples 29 to 32 give better results than the other solvents. Certain solvents (Examples 40 to 42) do not allow any esterification to be obtained.

EXAMPLE 43

Interesterification

The reaction mixture is constituted by tallow and sunflower oil in the weight ratio of 70/30 respectively, in 25% solution in trichlorotrifluoroethane vol/vol. The reactor is constituted by a column containing 5.5 g of the of devitalised mycelium *Rhizopus arrhizus* per 10 ml of silica, with preliminary dessication of the reaction medium on the molecular sieve. After a residence time of 60 mins, a rate of interesterification of 100% for a productivity of the order of 1.5 kg of interesterified fatty material/hour and per kg of dry mycelium is obtained, the operation being carried out continuously.

We claim:

1. In a process of carrying out an enzymatic reaction comprising contacting a substrate dissolved in an organic liquid solvent therefor with the enzyme, the improvement which comprises said solvent comprising a fluorinated hydrocarbon and the reaction is conducted in a non-aqueous environment.

2. Process according to claim 1 wherein the fluorinated hydrocarbon is trichlorotrifluoroethane, trichlorofluoromethane, tetrachlorofluorooctane or perfluoroheptane.

3. Process according to claim 1 in which the enzyme is selected from the group consisting of hydrolase, oxidase and transferase.

4. Process according to claim 1 wherein the enzyme is lipase.

5. Process according to claim 1, wherein the fluorinated hydrocarbon corresponds to the general formula $C_nH_mF_pX_t$, where n is 1 to 8, m is 0 to n, p is 1 to 18 and t is 0 to 16, and each X is individually Cl or Br.

6. Process according to claim 5, wherein the fluorinated compound boils below 100° C. and, in the formula, n is 1 to 4, m is 0 to n, p is 1 to 4 and t is 0 to 6.

7. Process according to claim 1 wherein the fluorinated hydrocarbon is employed in admixture with another organic liquid which is a hydrocarbon, alcohol, ester, ether or ketone.

8. Process according to claim 7 wherein the fluorinated hydrocarbon is 29-95% by weight of the admixture.

9. Process according to claim 1 wherein the enzymatic reaction is carried out on a fatty material in solution in the fluorinated hydrocarbon.

10. Process according to claim 9, in which the enzyme is selected from the group consisting of hydrolase, oxidase and transferase.

11. Process according to claim 9 wherein the enzyme is lipase.

12. Process according to claim 11 wherein the substrate is a fatty acid or ester.

13. Process according to claim 12 in which the enzymatic reaction is between the fatty acid or ester and an alcohol, amine, mercaptan, carboxylic acid or different fatty acid ester to effect an enzymatic esterification, amidation, thioesterification, transesterification, alcoholysis or interesterification and the reaction is carried out at a temperature of 10° to 50° C.

14. Process according to claim 13 wherein the fatty acid have 14 to 18 carbon atoms.

15. Process according to claim 13 wherein the enzyme is produced by the fungus Rhizopus arrhizus or Geotrichum candidum.

* * * * *